ated Mar. 8, 1988

United States Patent [19]
Minai et al.

[11] Patent Number: 4,729,953
[45] Date of Patent: * Mar. 8, 1988

[54] OPTICALLY ACTIVE 4-HYDROXY-2-CYCLOPENTENONES, AND THEIR PRODUCTION

[75] Inventors: Masayoshi Minai, Moriyama; Tadashi Katsura, Osaka, both of Japan

[73] Assignee: Sumitomo Chemical Company, Limited, Osaka, Japan

[*] Notice: The portion of the term of this patent subsequent to Apr. 16, 2002 has been disclaimed.

[21] Appl. No.: 680,533

[22] Filed: Dec. 11, 1984

Related U.S. Application Data

[63] Continuation-in-part of Ser. No. 575,588, Jan. 31, 1984, abandoned.

[30] Foreign Application Priority Data

Feb. 3, 1983 [JP] Japan .................................. 58-17054
Aug. 10, 1983 [JP] Japan .............................. 58-147155

[51] Int. Cl.⁴ .......................... C12P 7/38; C12P 41/00; C12R 1/38
[52] U.S. Cl. .................................. 435/149; 435/280; 435/874
[58] Field of Search .............. 435/148, 149, 157, 280, 435/874; 568/341, 347, 379

[56] References Cited

U.S. PATENT DOCUMENTS

| | | | |
|---|---|---|---|
| 3,931,291 | 1/1976 | Horiuchi | 568/379 X |
| 3,947,519 | 3/1976 | Matsui et al. | 568/346 |
| 4,005,146 | 1/1977 | Goffinet | 568/366 |
| 4,265,817 | 5/1981 | Martel et al. | 549/90 X |
| 4,347,386 | 8/1982 | Saito et al. | 568/341 X |
| 4,374,257 | 2/1983 | Martel et al. | 549/300 X |
| 4,511,655 | 4/1985 | Minai et al. | 435/280 X |

FOREIGN PATENT DOCUMENTS

| | | | |
|---|---|---|---|
| 22162 | 1/1981 | European Pat. Off. | 568/347 |
| 39089 | 11/1981 | European Pat. Off. | 568/347 |
| 115860 | 8/1984 | European Pat. Off. | 435/148 |
| 57-38741 | 3/1982 | Japan | 568/341 |
| 57-62236 | 4/1982 | Japan | 568/341 |
| 58-47495 | 3/1983 | Japan | 435/149 |

OTHER PUBLICATIONS

Derwent Abstract, 57298b/31, (1979).

*Primary Examiner*—Esther M. Kepplinger
*Attorney, Agent, or Firm*—Birch, Stewart, Kolasch & Birch

[57] ABSTRACT

A process for preparing an optically active 4-hydroxy-2-cyclopentenone of the formula:

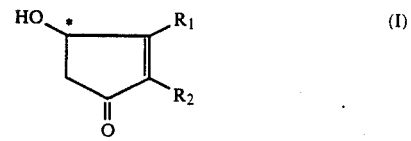

wherein $R_1$ is a hydrogen atom or a methyl group, $R_2$ is an alkyl group, an alkenyl group or an alkynyl group and the asterisk (*) indicates an asymmetric configuration, which comprises subjecting an optically active 4-cyclopentenone-alcohol of the formula:

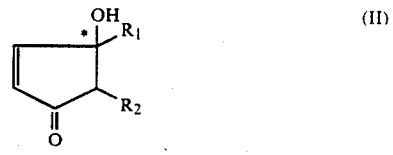

wherein $R_1$ and $R_2$ are each as defined above, the asterisk (*) indicates an asymmetric configuration and the substituents $R_1$ and $R_2$ take a cis-configuration to rearrangement while maintaining the original steric configuration.

27 Claims, No Drawings

OPTICALLY ACTIVE 4-HYDROXY-2-CYCLOPENTENONES, AND THEIR PRODUCTION

This is a continuation-in-part application of our co-pending application Ser. No. 575,588 filed Jan. 31, 1984, now abandoned.

The present invention relates to 4-hydroxy-2-cyclopentenones and their production. More particularly, it relates to a novel process for preparing optically active 4-hydroxy-2-cyclopentenones of the formula:

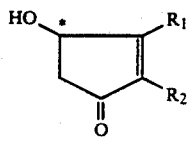
(I)

wherein $R_1$ is a hydrogen atom or a methyl group, $R_2$ is an alkyl group, an alkenyl group or an alkynyl group and the asterisk (*) indicates an asymmetric configuration. The terms "alkyl", "alkenyl" and "alkynyl" as hereinabove stated represent usually those having not more than 12 carbon atoms. Preferred are those having not more than 8 carbon atoms. Particularly preferred are those having not more than 6 carbon atoms. The substituent can represent not only non-cyclic ones but also cyclic ones, inclusively. Specific examples of possible groups are methyl, ethyl, n-propyl, isopropyl, n-butyl, sec-butyl, t-butyl, n-pentyl, n-hexyl, cyclopentyl, cyclohexyl, allyl, 2-butenyl, 3-butenyl, 2-pentynyl, n-hexenyl, etc. The 4-hydroxy-2-cyclopentenones (I) are per se useful as agricultural chemicals and also as intermediates in the synthesis of agricultural chemicals, pharmaceuticals, perfumes, etc. For instance, the 4-hydroxy-2-cyclopentenones (I) having the S-configuration can be used as the intermediates for the synthesis of pyrethroids which are important agricultural chemicals. Also, the 4-hydroxy-2-cyclopentenones (I) having the R-configuration can be utilized as the intermediates for the synthesis of prostaglandins.

Further, the 4-hydroxy-2-cyclopentenones (I) may be converted into their stereoisomers having the adverse configuration by reacting the former with p-toluenesulfonyl chloride or methanesulfonyl chloride and then reacting the resultant sulfonate with a base or by reacting the former with an alkali metal acetate or haloacetate (e.g. sodium acetate, sodium dichloroacetate, sodium trichloroacetate) and then hydrolyzing the resultant ester.

For preparation of the 4-hydroxy-2-cyclopentenones (I), there are known some procedures, of which typical examples are as follows:

(A) A procedure comprising reacting 2-substituted-4-hydroxy-3-methyl-2-cyclopentenone with a dicarboxylic acid (e.g. phthalic acid, succinic acid) or its reactive derivative and subjecting the resultant dicarboxylic acid half ester to optical resolution by the use of an optically active amine, followed by salt decomposition and hydrolysis (Japan Kokai Nos. 75545/1973 and 13366/1975);

(B) A procedure comprising subjecting a ketone to asymmetric reduction (Japan Kokai No. 79252/1979);

(C) A procedure comprising synthesizing an ether of dl-2-allyl-4-hydroxy-3-methyl-2-cyclopentenone and separating the ether into each optical isomer, followed by hydrolysis (Japan Kokai 130556/1979); and (D) A procedure comprising hydrolysing 4-acyloxy-2-allyl-3-methyl-2-cyclopentenone with an enzyme or a microorganism (Japan Kokoku No. 9917/1981), etc.

Among them, Procedure (A) requires not only an expensive amine for the reaction but also takes many and troublesome operation steps. Similarly, Procedures (B) and (C) necessitate expensive reagents and complex operations. In addition, the yield of the desired product is not good. It is uncertain whether Procedure (D) is generally applicable. Further, the produced R(-)-2-allyl-4-hydroxy-3-methyl-2-cyclopentenone is not satisfactory in optical purity. Furthermore, its R(+)-isomer, which is an important intermediate in the systhesis of pyrethroids, can be obtained only in the form of an ester, and hydrolysis with methanol/sodium methoxide is inevitably required. None of said conventional procedures is thus satisfactory for industrial application.

As a result of the extensive study, it has now been found that the optically active 4-hydroxy-2-cyclopentenone (I) can be prepared with a high purity and a good yield in an industrially advantageous manner by subjecting an optically active 4-cyclopentenone-alcohol of the formula:

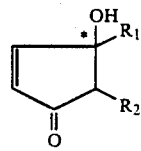
(II)

wherein $R_1$ and $R_2$ are each as defined above, the asterisk (*) indicates an asymmetric configuration and the substituents $R_1$ and $R_2$ take a cis-configuration to rearrangement.

The optically active 4-cyclopentenone-alcohol (II) may be prepared, for instance, by subjecting the racemic or optically active 4-cyclopentenone ester of the formula:

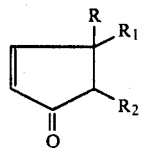
(III)

wherein $R_1$ and $R_2$ are each as defined above, R is an acyloxy group such as lower alkanoyloxy (e.g. acetoxy, propionyloxy, butyryloxy) and the substituents $R_1$ and $R_2$ take a cis-configuration to asymmetric hydrolysis with an enzyme or microorganism. As a practical modification, the above conversion may be accomplished by subjecting the racemic 4-cyclopentenone ester (III) to asymmetric hydrolysis with an enzyme or microorganism, separating the unhydrolyzed optically active 4-cyclopentenone ester (III) from the reaction mixture and hydrolyzing the recovered unhydrolyzed optically active 4-cyclopentenone ester (III) with a microorganism or an enzyme to give the optically active 4-cyclopentenone-alcohol (II).

The racemic 4-cyclopentenone ester (III) is obtainable by esterifying the racemic 4-cyclopentenone-alcohol (II) with an aliphatic carboxylic acid or its reactive derivative by a per se conventional procedure.

Among the intermediary compounds as mentioned above, the optically active 4-cyclopentenone ester (III) as well as the optically active 4-cyclopentenone-alcohol (II) are novel.

The process of this invention will be explained below more in detail.

First, the racemic 4-cyclopentenone-alcohol (II) is reacted with an aliphatic carboxylic acid or its reactive derivative to give the 4-cyclopentenone ester (III).

The racemic 4-cyclopentenone-alcohol (II) is one of the starting materials can be prepared, for instance, by rearrangement of the corresponding furan-carbinol of the formula:

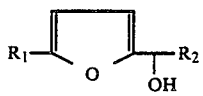

wherein $R_1$ and $R_2$ are each as defined above. Specific example of the racemic 4-cyclopentenone-alcohol (II) are as follows: 3-hydroxy-2-methyl-4-cyclopentenone, 2-ethyl-3-hydroxy-4-cyclopentenone, 3-hydroxy-2-n-propyl-4-cyclopentenone, 2-isopropyl-3-hydroxy-4-cyclopentenone, 3-hydroxy-2-n-butyl-4-cyclopentenone, 2-isobutyl-3-hydroxy-4-cyclopentenone, 3-hydroxy-2-hydroxy-2-n-pentyl-4-cyclopentenone, 3-hydroxy-2-n-hexyl-4-cyclopentenone, 3-hydroxy-2-n-heptyl-4-cyclopentenone, 2-allyl-3-hydroxy-4-cyclopentenone, 2-(2-cis-butenyl)-3-hydroxy-4-cyclopentenone, 2-(ω-butenyl)-3-hydroxy-4-cyclopentenone, 2-(2-cis-pentenyl)-3-hydroxy-4-cyclopentenone, 3-hydroxy-2-(2-trans-pentenyl)-4-cyclopentenone, 2-(3-cis-hexenyl)-3-hydroxy-4-cyclopentenone, 3-hydroxy-2-proparyl-4-cyclopentenone, 3-hydroxy-2-(2-pentynyl)-4-cyclopentenone, 3-hydroxy-2-(α-methylallyl)-4-cyclopentenone, 3-hydroxy-2,3-dimethyl-4-cyclopentenone, 2-ethyl-3-hydroxy-3-methyl-4-cyclopentenone, 3-hydroxy-2-n-propyl-3-methyl-4-cyclopentenone, 2-isopropyl-3-hydroxy-3-methyl-4-cyclopentenone, 3-hydroxy-2-n-butyl-3-methyl-4-cyclopentenone, 2-isobutyl-3-hydroxy-3-methyl-4-cyclopentenone, 3-hydroxy-2-n-pentyl-3-methyl-4-cyclopentenone, 2-isopentyl-3-hydroxy-3-methyl-4-cyclopentenone, 3-hydroxy-2-n-hexyl-3-methyl-4-cyclopentenone, 3-hydroxy-2-cyclopentyl-3-methyl-4-cyclopentenone, 2-allyl-3-hydroxy-3-methyl-4-cyclopentenone, 2-(2-cis-butenyl)-3-hydroxy-3-methyl-4-cyclopentenone, 2-(ω-butenyl)-3-hydroxy-3-methyl-4-cyclopentenone, 2-(2-cis-pentenyl)-3-hydroxy-3-methyl-4-cyclopentenone, 3-hydroxy-2-(2-trans-pentenyl)-3-methyl-4-cyclopentenone, 2-(3-cis-hexenyl)-3-hydroxy-3-methyl-4-cyclopentenone, 3-hydroxy-2-propargyl-3-methyl-4-cyclopentenone, 3-hydroxy-2-(2-pentynyl)-3-methyl-4-cyclopentenone, 3-hydroxy-2-(α-methylallyl)-3-methyl-4-cyclopentenone, etc.

The other starting material is an aliphatic carboxylic acid or its reactive derivative. As the reactive derivative, there may be used acid halide, acid anhydride, etc. Specific examples of the aliphatic carboxylic acid and its reactive derivative are acetic acid, acetyl chloride, acetyl bromide, acetic anhydride, propionic acid, propionyl chloride, propionyl bromide, propionic anhydride, butyryl chloride, butyryl bromide, caproyl chloride, caproyl bromide, capryloyl chloride, capryloyl bromide, caprinoyl chloride, caprinoyl bromide, dodecanoyl chloride, dodecanoyl bromide, palmitoyl chloride, palmitoyl bromide, chloroacetyl chloride, chloroacetyl bromide, dichloroacetyl chloride, dichloroacetyl bromide, etc.

The reaction may be carried out under the conditions as conventionally adopted for esterification, for instance, in the presence or absence of an inert solvent in the existence of a catalyst. Examples of the inert solvent are ethers (e.g. tetrahydrofuran, ethyl ether), ketones (e.g. acetone, methyl ethyl ketone), hydrocarbons (e.g. hexane, toluene, benzene), halogenated hydrocarbons (e.g. chlorobenzene, dichloromethane, dichloroethane, chloroform, carbon tetrachloride), dimethylformamide, etc. The solvent may be used alone or in combination, and no particular limitation is present on its amount.

The aliphatic carboxylic acid or its reactive derivative may be used in an amount of not less than one equivalent, preferably from 1 to 4 equivalents, to the racemic 4-cyclopentenone-alcohol (II), although there is no particular limitation on its upper limit.

As the catalyst, there may be used any organic or inorganic base such as triethylamine, tri-n-butylamine, pyridine, picoline, sodium carbonate, sodium methoxide or potassium hydrogencarbonate. The amount of the catalyst is not limitative, and it may be usually from 1 to 5 equivalents to the racemic 4-cyclopentenone-alcohol (II). When an organic amine in a liquid state is used as the solvent, it can simultaneously serve as the catalyst. Instead of the base, an acid such as p-toluenesulfonic acid or methanesulfonic acid may be also employed as the catalyst.

The reaction temperature is usually from −20° to 150° C., preferably from −10° to 120° C. Any limit is not present on the reaction time.

As the result of the above reaction, there is produced the racemic 4-cyclopentenone ester (III) in a good yield. Its recovery from the reaction mixture may be accomplished by a per se conventional separation procedure such as extraction, fractionation, concentration or listillation. Alternatively, the racemic 4-cyclopentenone ester (III) may be employed as such in the next step without separation from the reaction mixture.

In the next step, the 4-cyclopentenone ester (III) is treated with an enzyme or microorganism capable of hydrolyzing the same, whereby either one of the optical isomers is selectively hydrolyzed to give the optically active 4-cyclopentenone-alcohol (II). Thus, the 4-cyclopentenone ester (III) as the starting material in this step is not necessarily limited to the racemic one as produced in the preceding step and may be in the racemic form, in the optically active form or in a mixture including one of the optical isomers excessively in comparison with the other optical isomer.

As the enzyme, there may be used anyone obtainable from animals, plants, microorganisms, etc. The enzyme may be employed in any conventional form such as a purified form, a crude form, a mixture with other enzymes, a microbial fermentation broth, a fermentation broth, a microbial body, a filtrate of fermentation broth, etc. These may be employed solely or in combination. Further, such enzyme or microbial body as immobilized on a resin is also employable. Specific examples of the enzyme are those obtainable from animals and plants such as cow liver esterase, pig liver esterase, pig pancreas esterase, horse liver esterase, dog liver esterase, pig phosphatase, β-amylase obtainable from barley and potato and lipase obtainable from wheat. Other examples are hydrolases obtainable from such microorganisms as Rhodotorula, Trichoderma, Candida, Hansenula, Pseudomonas, Bacillus, Achromobacter, Nocardia, Chromobacterium, Flavobacterium, Rhizopus, Mucor, Aspergillus, Alkaligenes, Torulopsis, Corynebacterium, Endomyces, Saccaromyces, Arthrobacter, Metshnikowia, Pleurotus, Streptomyces, Proteus, Gliocladium, Acetobacter, Helminthosporium, Brevibacterium, Escherichia, Citrobacter, Absidia, Micrococcus, Pediococcus, Klebsiella, Geotrichum, Lactobaccilus, Cryptococcus, Pichia, Aureobasidium, Actinomucor, Enterobacter, Microbacterium, Penicillium, etc. as well as from lichen, algae, etc. Specific example of the microorganisms are *Rhodotorula minuta* (IFO-0387, IFO-0412), *Rhodotorula rubra* (IFO-0870), *Rhodotolura minuta var. texensis* (IFO-0879), *Trichoderma longibrachiatum* (IFO-4847), *Mucor javanicus* (IFO-4572), *Streptomyces grisens* (IFO-3356), *Micrococcus luteus* (IFO-3066), *Enterobacter cloacae* (IFO-3320), *Corynebacterium ezui* (ATCC-7699), *Lacto bacillus casei* (IFO-3322), *Cryptoccus albidus* (IFO-0378), *Pichia polimorpha* (IFO-1166), *Penicillium frezuentans* (IFO-5692), *Aureobasidium pullulans* (IFO-4464), *Actinomucor elegans* (IFO-4022), *Candida krusei* (OUT-6007), *Candida cylindracea*, *Candida tropicalis* (PK-233), *Candida utilus* (IFO-1086), *Pseudomonas fragi* (IFO-3458), *Pseudomonas putida* (IFO-12996), *Pseudomonas fluorescens* (IFO-3903), *Pseudomonas aeruginosa* (IFO-080), *Hansenula anomala var. ciferrii* (OUT-6095), *Hansenula anomala* (IFO-0118), *Hansenula polymorpha* (IFO-1475), *Bacillus cereus* (IFO-3466), *Bacillus subtilis* (ATCC-6638), *Bacillus pulmilus* (IFO-12092), *Bacillus subtilis var. niger* (IFO-3108), *Achromobacter lyticus* (ATCC-21456), *Achromobacter parvulus* (IFO-13181), *Achromobacter sinplex* (IFO-12069), *Nocardia uniformis subtsuyanarenus* (ATCC-21806), *Nocardia uniformis* (IFO-13072), *Chromobacterium chocolatum* (IFO-3758), *Chromobacterium iodinum* (IFO-3558), *Chromobacterium violaceum* (IFO-12614), *Flavobacterium lutescens* (IFO-3084), *Flavobacterium arbonescens* (IFO-3750), *Flavobacterium heparinum* (IFO-12017), *Flavobacterium capsulatum* (IFO-12533), *Rhizopus chinensis* (IFO-4768), *Mucor pusillus* (IFO-9856), *Aspergillus niger* (ATCC-9642), *Alkaligenes faecalis* (IFO-12669), *Torulopsis ernobii* (IFO-0654), *Torulopsis candida* (IFO-0768), *Corynebacterium sepedonicum* (IFO-13763), *Endomyces geotrichum* (IFO-9542), *Saccaromyces carrvisial* (IFO-0334), *Arthrobacter globiformis* (IFO-12137), *Metschnikowia pulcherrima* (IFO-0561), *Pleurotus ostreatus* (IFO-7051), *Streptomyces grisens* (IFO-3356), *Proteus vulgaris* (IFO-3851), *Proteus vulgaris* (IID-874), *Gliocladium roseum* (IFO-5422), *Gliocladium virens* (IFO-6355), *Acetobacter aurantius* (IFO-3247), *Helminthosporium sp.* (ATCC-20154), *Brevibacterium ammoniagenes* (IFO-12072), *Brevibacterium divaricatum* (ATCC-14020), *Escherichia coli* (IFO- 12713, IFO-3302, IFO-13168), *Citrobacter freundii* (IFO-12681), *Micrococcus varians* (IFO-3765), *Micrococcus luteus* (IFO-3066), *Pediococcus acidlactici* (IFO-3076), *Klebsiella pneumoriae* (IFO-12059), *Absidia hyalospora* (IFO-8082), *Geotrichun candidum* (IFO-4597), etc.

Instead of the enzyme, there may be employed a microorganism which can produce any enzyme as stated above.

The enzyme or microorganism may be used alone or in combination. Depending upon the kind of the enzyme or microorganism as used, either one of the optical isomers of the 4-cyclopentenone ester (III), particularly when $R_1$ is $CH_3$, is predominantly hydrolyzed to give the optically active 4-cyclopentenone-alcohol (II). Thus, it is a great characteristic of this invention that either one of the optical isomers is optionally obtained by selection of a suitable enzyme or microorganism.

Since asymmetric reduction is hardly applicable to tertiary alcohols, the production of the optically active forms of the 4-cyclopentenones is extremely difficult. Quite surprisingly, the asymmetric hydrolysis in the process of this invention can accomplish the hydrolysis of the 4-cyclopentenone esters with a good optical purity. Further, either of the d-form and the l-form is optionally obtainable by application of such asymmetric hydrolysis.

For selective hydrolysis of the d-4-cyclopentenone ester (III) giving the l-4-cyclopentenone-alcohol (II), any one chosen from the following enzymes or microorganisms may be preferably employed: pig liver esterase, *Candida cylindracea, Hansenula anomala var. ciferrii* (OUT-6095), *Metshnikowia pulcherrima* (IFO-0561), *Pleurotus ostreatus* (IFO-7051), cholesterol esterase (from *Schizophyllum commune*), *Candida krusei* (OUT-6007), etc. For selective hydrolysis of the l-4-cyclopentenone ester (III) giving the d-4-cyclopentenone-alcohol (II), the use of any one chosen from the following enzymes or microorganisms is preferred: *Pseudomonas fragi* (IFO-3458), *Pseudomonas fluorescens* (IFO-3903), *Pseudomonas aeruginosa* (IFO-3080), etc. For instance, in case of using a microorganism belonging to Pseudomonas or an enzyme produced thereby, only the l-isomer in the 4-cyclopentenone ester (III) is hydrolyzed to the d-4-cyclopentenone-alcohol (II) leaving the d-isomer in the 4-cyclopentenone ester (III) as such. Further, for instance, in case of using a microorganism belonging to Candida or an enzyme produced thereby, only the d-isomer in the 4-cyclopentenone ester (III) is hydrolyzed to the l-4-cyclopentenone-alcohol (II) leaving the l-isomer in the 4-cyclopentenone ester (III) as such.

When $R_1$ in the formula (III) is a hydrogen atom, the hydrolysis with lipase generally affords the l-4-cyclopentenone-alcohol (II), resulting from the hydrolysis of the l-4-cyclopentenone ester (III), and the unreacted d-4-cyclopentenone ester. Therefore, in order to obtain the d-4-cyclopentenone-alcohol (II), it is necessary first to separate the unreacted d-4-cyclopentenone ester (III) from the reaction mixture and then hydrolyze this d-4-cyclopentenone ester (III) with an enzyme or microorganism capable of hydrolyzing such d-4-cyclopentenone ester (III).

Cultivation of the microorganism may be carried out in an appropriate nutrient medium according to a per se conventional procedure to obtain a culture. For instance, the microorganism may be inoculated in a sterilized liquid nutrient medium, followed by cultivation at a temperature of 20° to 40° C. for 1 to 3 days while reciprocal shaking. Examples of the liquid nutrient medium are a malt extract-yeast extract medium comprising peptone (5 g), glucose (10 g), malt extract (3 g) and yeast extract (3 g) in water (1000 ml) and adjusted to pH 6.5 (suitable for fungi and yeasts), a saccharide-added bouillon medium comprising glucose (10 g), peptone (5 g), meat extract (5 g) and sodium chloride (3 g) in water (1000 ml) and adjusted to pH 7.2 (suitable for bacteria), etc. In place of a liquid medium, a solid medium is also usable.

Among esterases originated from a microorganism, there are included those available on the market, of which examples are lipase obtained from Pseudomonas (manufactured by Amano Pharmaceutical Co., Ltd.), lipase obtained from Aspergillus ("Lipase AP" manufactured by Amano Pharmaceutical Co., Ltd.), lipase obtained from Mucor ("Lipase M" manufactured by Amano Pharmaceutical Co., Ltd.), lipase obtained from Candida cylindracea ("Lipase MY" manufactured by Meito Sangyo), lipase obtained from Alkaligenes ("Lipase PL" manufactured by Meito Sangyo), lipase obtained from Acromobacter ("Lipase AL" manufactured by Meito Sangyo), lipase obtained from Arthrobacter ("Lipase Godo BSL" manufactured by Godo Shusei), lipase obtained from Chromobacterium (manufactured by Toyo Jozo), lipase obtained from Rhizopus delemer ("Talipase" manufactured by Tanabe Pharmaceutical Co., Ltd.), lipase obtained from Rhizopus ("Lipase Saiken" manufactured by Osaka Saikin Kenkyusho), etc.

The asymmetric hydrolysis may be carried out by contacting the 4-cyclopentenone ester (III), which may be racemic or contain optionally either one of the optical isomers in an excessive amount, with the enzyme or microorganism as stated above, usually in a buffer medium while stirring vigorously. As the buffer medium, there may be employed inorganic acid salt buffers (e.g. sodium phosphate, potassium phosphate), organic acid salt buffers (e.g. sodium citrate), etc. These buffers have normally a pH of 4 to 10, preferably of 5 to 9. The concentration of the buffer may be from 0.05 to 2 M, preferably from 0.05 to 0.5 M. The reaction temperature may be ordinarily from 20° to 40° C., and the reaction time is generally from 10 to 70 hours.

In order to achieve a better optical yield in the asymmetric hydrolysis, it is preferred to interrupt the hydrolysis at an appropriate stage depending upon the optical composition of the starting material. When, for instance, the racemic 4-cyclopentenone ester (III) is used, the hydrolysis is favorably finished with a reaction rate of less than 50%.

For recovery and separation of the hydrolyzed and unhydrolyzed optional isomers from the reaction mixture, it may be, for instance, extracted with an appropriate solvent (e.g. methyl isobutyl ketone, ethyl acetate, ethyl ether). The extract is then concentrated, and the residue is purified, for instance, by column chromatography to isolate the hydrolyzed product, i.e. the optically active 4-cyclopentenone-alcohol (II), and the unhydrolyzed product, i.e. the optically active 4-cyclopentenone ester (III), separately. The unhydrolyzed product as collected may be then subjected to hydrolysis to obtain the corresponding optically active hydrolyzed product. When desired, the thus obtained optically hydrolyzed product may be used as the starting material for production of the adverse optical isomer.

On the asymmetric hydrolysis as above, a portion of the produced 4-cyclopentenone-alcohol (II) may be simultaneously epimerized at the 2-position to give the compounds of the formulas:

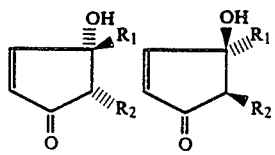

wherein the substituents at the 2- and 3-positions take a trans-configuration. However, these by-products need not be eliminated, because they can be subjected to rearrangement together with the major hydrolyzed product to give the optically active 4-hydroxy-2-cyclopentenone (I) having the same steric configuration as that of the product from the latter.

The l-4-cyclopentenone ester (III) and the d-4-cyclopentenone-alcohol (II) as stated above are useful not only for production of the objective optically active 4-hydroxy-2-cyclopentenone (I) but also for production of racemic 2-substituted-3-unsubstituted or methyl-4-cyclopentenone by heating with acetic acid and sodium acetate for rearrangment with racemization to racemic 2-substituted-3-unsubstituted or methyl-4-acetoxy-4-cyclopentenone, which is then hydrolyzed.

Further, it may be noted that the optically active 4-cyclopentenone-alcohol (II) is per se novel. As to the 4-cyclopentenone-alcohol (II) in the racemic form, it is reported in Tetrahedron Letter, No. 39, 3555–3558 (1976) and Tetrahedron, Vol. 34, 2775 (1978)) that the racemic product is a mixture of the following isomers ($A_1$) and ($A_2$):

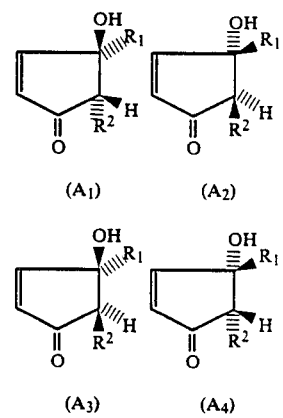

However, said literatures are entirely silent on the separation of such racemic mixture into each isomer as well as the physical and chemical properties of each optical isomer. They are also silent on such advantageous characteristic feature of each optical isomer as can be rearranged while retaining its steric configuration and on the steric configuration of the 4-hydroxy-2-cyclopentenones (I) resulting from said rearrangement.

The above obtained optically active 4-cyclopentenone-alcohol (II) is then subjected to rearrangement in the presence of a catalyst while maintaining the steric configuration to give the objective optically active 4-hydroxy-2-cyclopentenone (I).

When $R_1$ in the formula (II) is a methyl group, rearrangement of the l-4-cyclopentenone-alcohol (II) gives the 4-hydroxy-2-cyclopentenone (I) having the S(+)-configuration, which is quite useful as an intermediate in the production of pyrethroids. Similarly, rearrangement of the d-4-cyclopentenone-alcohol (II) affords the 4-hydroxy-2-cyclopentenone (I) having the R(−)-configuration, which is useful as an intermediate in the production of prostaglandins.

When $R_1$ in the formula (II) is a hydrogen atom, rearrangement of the l-4-cyclopentenone-alcohol (II) gives the 4-hydroxy-2-cyclopentenone (I) having the R(+)-configuration, which is useful as an intermediate in the synthesis of prostaglandins.

The rearrangment of the optically active 4-cyclopentenone-alcohol (II) is thus desired to be accomplished while keeping the optical purity as high as possible, i.e. with suppressing racemization, by selecting suitable catalysts and appropriate reaction conditions.

Normally, the rearrangment is effected in an inert solvent in the presence of a catalyst. As the inert solvent, there may be exemplified water, aliphatic or aromatic hydrocarbons, halogenated hydrocarbons, ethers, ketones, esters, etc. More specifically, tetrahydrofuran, dioxane, acetone, benzene, toluene, ethyl acetate, chlorobenzene, heptane, dichloromethane, dichloroethane, diethyl ether, cyclohexane, etc. and their mixtures are exemplified. Examples of the catalyst are organic tertiary amines (e.g. triethylamine, N-methylmorpholine, N-methylpiperidine, N,N'-dimethylpiperidine, pyridine, lutidine), metallic oxides (e.g. alumina, silica gel), inorganic bases (e.g. sodium hydroxide, potassium hydroxide, sodium carbonate, potassium carbonate, sodium hydrocarbon, dipotassium hydrogen-phosphate), basic buffers (e.g. carbonate buffer, phosphate buffer and borate buffer), etc. These may be solely or in combination.

There is no particular limitation on the amount of the catalyst, and it is generally employed in an amount of 0.05 to 60 moles to one mole of the optically active 4-cyclopentenone alcohol (II).

The reaction temperature may be normally from −20° to 130° C., although it may appropriately be adjusted depending upon the kinds of the solvent and the catalyst. For instance, in a non-aqueous medium, racemization hardly occurs so that the reaction may be effected at a temperature of −10° to 130° C. In case of using an aqueous medium such as a mixture of water and an organic tertiary amine as the solvent, the reaction may be favorably effected at a temperature of −10° to 90° C. When the reaction is effected in water or under a strongly basic condition, the temperature is preferred from −20° to 50° C. The reaction time is not limitative.

Recovery of the optically active 4-hydroxy-2-cyclopentenone (I) may be accomplished by a per se conventional separation procedure such as extraction, fractionation, concentration or distillation. The optical purity and the yield are usually excellent.

Examples of the optically active 4-hydroxy-2-cyclopentenone (I) having the R- or S-configuration as thus produced are as follows: 4-hydroxy-2,3-dimethyl-2-cyclopentenone, 2-ethyl-4-hydroxy-3-methyl-2-cyclopentenone, 4-hydroxy-2-n-pentyl-3-methyl-2-cyclopentenone, 2-isopropyl-4-hydroxy-3-methyl-2-cyclopentenone, 4-hydroxy-2-n-butyl-3-methyl-2-cyclopentenone, 2-isobutyl-4-hydroxy-3-methyl-2-cyclopentenone, 4-hydroxy-2-n-pentyl-3-methyl-2-cyclopentenone, 2-isopentyl-4-hydroxy-3-methyl-2-cyclopentenone, 2-cyclopentyl-4-hydroxy-3-methyl-2-cyclopentenone, 4-hydroxy-2-n-hexyl-3-methyl-4-cyclopentenone, 4-hydroxy-2-n-heptyl-3-methyl-2-cyclopentenone, 2-allyl-4-hydroxy-3-methyl-2-cyclopentenone, 2-(2-cis-butenyl)-4-hydroxy-3-methyl-2-cyclopentenone, 4-hydroxy-2-(ω-butynyl)-3-methyl-2-cyclopentenone, 2-(2-cis-pentenyl)-4-hydroxy-3-methyl-2-cyclopentenone, 4-hydroxy-(2-trans-pentenyl)-3-methyl-2-cyclopentenone, 2-(3-cis-hexenyl)-4-hydroxy-3-methyl-2-cyclopentenone, 4-hydroxy-2-propargyl-3-methyl-2-cyclopentenone, 4-hydroxy-2-(2-pentynyl)-3-methyl-4-cyclopentenone, 4-hydroxy-2-(2-methylallyl)-3-methyl-2-cyclopentenone, 4-hydroxy-2-methyl-2-cyclopentenone, 2-ethyl-4-hydroxy-2-cyclopentenone, 4-hydroxy-2-n-propyl-2-cyclopentenone, 2-isopropyl-4-hydroxy-2-cyclopentenone, 4-hydroxy-2-n-butyl-2-cyclopentenone, 2-isobutyl-4-hydroxy-2-cyclopentenone, 4-hydroxy-2-n-pentyl-2-cyclopentenone, 2-isopentyl-4-hydroxy-2-cyclopentenone, 4-hydroxy-2-n-hexyl-4-cyclopentenone, 4-hydroxy-2-n-heptyl-2-cyclopentenone, 2-allyl-4-hydroxy-2-cyclopentenone, 2-(2-cis-butenyl)-4-hydroxy-2-cyclopentenone, 4-hydroxy-2-(ω-butenyl)-2-cyclopentenone, 2-(2-cis-pentenyl)-4-hydroxy-2-cyclopentenone, 4-hydroxy-(2-trans-pentenyl)-2-cyclopentenone, 2-(3-cis-hexenyl)-4-hydroxy-2-cyclopentenone, 4-hydroxy-2-propargyl-2-cyclopentenone, 4-hydroxy-2-(2-pentynyl)-4-cyclopentenone, 4-hydroxy-2-(2-methylallyl)-2-cyclopentenone, etc.

Practical and presently preferred embodiments of the invention are illustratively shown in the following Examples wherein part(s) and % are by weight unless otherwise indicated.

EXAMPLE 1

Into a flask equipped with a stirrer and a thermometer, dl-2-allyl-3-hydroxy-3-methyl-4-cyclopentenone (152 g), p-toluenesulfonic acid (1 g) and acetic anhydride (320 g) were charged, and the resultant mixture was stirred at 100° C. for 2 hours. After completion of the reaction, acetic anhydride was removed under reduced pressure, and the residue was extracted with toluene. The toluene layer was washed with 1% sodium bicarbonate solution and water in order. Toluene was removed from the toluene layer to give dl-3-acetoxy-2-allyl-3-methyl-4-cyclopentenone (186 g). Yield, 96%. B.P., 72°–75° C./0.2–0.3 mmHg.

The thus obtained dl-3-acetoxy-2-allyl-3-methyl-4-cyclopentenone (5 g), Porcine Liver Esterase (manufactured by Sigma Inc.) (300 mg) and 0.1 M phosphate buffer (200 ml; pH 7.0) were mixed together, and the resultant mixture was stirred at 25°–30° C. for 24 hours. After completion of the reaction, the reaction mixture was extracted with methyl isobutyl ketone (50 ml) three times. The solvent was removed from the extract, and the residue was purified by column chromatography using a mixture of ethyl acetate and toluene (3:5) as an eluent to give 1.84 g of l-2-allyl-3-hydroxy-3-methyl-4-cyclopentenone (yield, 47%; optical rotation, $[\alpha]_D^{20}$ −23.9° (c=1, chloroform); $n_D^{20}$ 1.4983) and 2.5 g of l-3-acetoxy-2-allyl-3-methyl-4-cyclopentenone (optical rotation, $[\alpha]_D^{20}$ −91.8° (c=1, chloroform); $n_D^{20}$ 1.4801).

The above obtained l-2-allyl-3-hydroxy-3-methyl-4-cyclopentenone (0.5 g), alumina (10 g) and benzene (30 ml) were mixed together while stirring at 50°–60° C. for 6 hours. Alumina was collected by filtration and washed with methanol (10 ml) twice. The filtrate was concentrated, and the residue was purified by column chromatography using a mixture of toluene and ethyl acetate (5:2) to give 0.43 g of S(+)-2-allyl-4-hydroxy-3-methyl-2-cyclopentenone. Optical purity, 98% (determind by the method as described in Agr. Biol. Chem., 41 (10), 2003–2006 (1977)). Optical rotation, $[\alpha]_D^{20}$ +15.3° (c=1, chloroform). $n_D^{20}$ 1.5166.

EXAMPLE 2

Into the same flask as used in Example 1, dl-3-hydroxy-2-(ω-butenyl)-3-methyl-4-cyclopentenone (16.6 g), pyridine (0.2 g) and acetic anhydride (35 g) were charged, and the resultant mixture was stirred at 100°–120° C. for 3 hours. After completion of the reaction, the reaction mixture was subjected to the same work-up as in Example 1, followed by purification to give 19.9 g of dl-3-acetoxy-2-(ω-butenyl)-3-methyl-4-cyclopentenone. Yield, 96%. B.P., 81°–85° C./0.2 mmHg).

The thus obtained dl-3-acetoxy-2-(ω-butenyl)-3-methyl-4-cyclopentenone (2 g), Porcine Liver Esterase (manufactured by Sigma Inc.) (80 mg) and 0.1 M phosphate buffer (100 ml; pH 8) were mixed together, and the resultant mixture was vigorously stirred at 25°–30° C. for 24 hours. After completion of the reaction, the reaction mixture was extracted with methyl isobutyl ketone (40 ml) three times. The same work-up as in Example 1 gave 0.68 g of l-3-hydroxy-2-(ω-butenyl)-3-methyl-4-cyclopentenone (yield, 42.6%; optical rotation, $[α]_D^{20}$ −22.5° (c=1, chloroform); $n_D^{20}$ 1.4992) and 0.97 g of 1-3-acetoxy-2-ω-butenyl-3-methyl-4-cyclopentenone (optical rotation, $[α]_D^{20}$ −84.6° (c=1, chloroform); $n_D^{20}$ 1.4810).

The above obtained l-3-hydroxy-2-(ω-butenyl)-3-methyl-4-cyclopentenone (0.5 g), triethylamine (1 g), alumina (10 g) and benzene (30 ml) were mixed together while stirring at 50°–60° C. for 6 hours. Alumina was collected by filtration and washed with methanol (10 ml) twice. The filtrate was concentrated, and the residue was purified by column chromatography using a mixture of toluene ard ethyl acetate (5:2) to give 0.45 g of S(+)-4-hydroxy-2-ω-butenyl-3-methyl-2-cyclopentenone. Optical purity, 98.1%. Optical rotation, $[α]_D^{20}$ +14.8° (c=1, chloroform). $n_D^{20}$ 1.5174.

EXAMPLE 3

Into the same flask as used in Example 1, dl-3-hydroxy-2-propargyl-3-methyl-4-cyclopentenone (30 g) and acetic anhydride (70 g) were charged, and the resultant mixture was stirred at 100°–120° C. for 3 hours. After completion of the reaction, the reaction mixture was subjected to the same work-up as in Example 1 to give 36.4 g of dl-3-acetoxy-2-propargyl-3-methyl-4-cyclopentenone. Yield, 95%. B.P., 82°–86° C./0.2–0.3 mmHg).

The thus obtained dl-3-acetoxy-2-propargyl-3-methyl-4-cyclopentenone (2 g), Porcine Liver Esterase (manufactured by Sigma Inc.) (80 mg) and 0.1 M phosphate buffer (80 ml; pH 6) were mixed together, and the resultant mixture was vigorously stirred at 35° C. for 20 hours. After completion of the reaction, the reaction mixture was extracted with methyl isobutyl ketone (40 ml) three times. The same work-up as in Example 1 gave 0.72 g of l-3-hydroxy-3-methyl-2-propargyl-4-cyclopentenone (yield, 46.1%; optical 3 rotation, $[α]_D^{20}$ −131.7° (c=1, chloroform); M.P., 61° C.) and 0.96 g of l-3-acetoxy-2-propargyl-3-methyl-4-cyclopentenone (optical rotation, $[α]_D^{20}$ −16.2° (c=1, chloroform); $n_D^{20}$ 1.4943).

The above obtained l-3-hydroxy-2-propargyl-3-methyl-4-cyclopentenone (0.5 g) was adsorbed on a silica gel column (20 g) using a mixture of toluene and ethyl acetate (5:2). Twenty-four hours thereafter, the adsorbed material was extracted with the same mixture as above, followed by purification to give 0.30 g of S(+)-4-hydroxy-2-propargyl-3-methyl-2-cyclopentenone, which crystallized upon allowing to stand. Optical purity, 97.5%. Optical rotation, $[α]_D^{20}$ +21.4° (c=1, chloroform). $n_D^{20}$ 1.5311.

EXAMPLE 4

Into the same flask as used in Example 1, dl-3-hydroxy-2-n-pentyl-3-methyl-4-cyclopentenone (18.2 g), triethylamine (0.1 g) and acetic anhydride (36 g) were charged, and the resultant mixture was stirred at 60°–80° C. for 3 hours. After completion of the reaction, the reaction mixture was subjected to the same work-up as in Example 1 to give 21.9 g of dl-3-acetoxy-2-n-pentyl-3-methyl-4-cyclopentenone. Yield, 98%. B.P., 100°–110° C./0.1–0.3 mmHg).

The thus obtained dl-3-acetoxy-2-n-pentyl-3-methyl-4-cyclopentenone (2 g), Porcine Liver Esterase (manufactured by Sigma Inc.) (100 mg), 0.1 M phosphate buffer (90 ml; pH 7) and methanol (10 ml) were mixed together, and the resultant mixture was vigorously stirred at 35° C. for 20 hours. After completion of the reaction, the reaction mixture was extracted with toluene (30 ml) twice. The same work-up as in Example 1 gave 0.7 g of l-3-hydroxy-2-n-pentyl-3-methyl-4-cyclopentenone (yield, 43.1%; optical rotation, $[α]_D^{20}$ −18.4° (c=1, chloroform); $n_D^{20}$ 1.4818 and 1.04 g of l-3-acetoxy-2-n-pentyl-3-methyl-4-cyclopentenone (optical rotation, $[α]_D^{20}$ −69.4° (c=1, chloroform); $n_D^{20}$ 1.4708).

The above obtained l-3-hydroxy-2-n-pentyl-3-methyl-4-cyclopentenone (0.5 g), triethylamine (2 g), alumina (10 g) and benzene (30 ml) were mixed together while stirring at 60°–70° C. for 6 hours. The same work-up as in Example 2 gave 0.44 g of S(+)-4-hydroxy-2-n-pentyl-3-methyl-2-cyclopentenone. Optical purity, 97%. $[α]_D^{20}$ +17.9° (c=1, chloroform). $n_D^{20}$ 1.4888.

EXAMPLE 5

Into the same flask as used in Example 1, dl-3-hydroxy-2,3-dimethyl-4-cyclopentenone (12.6 g), p-toluenesulfonic acid (0.5 g) and acetic anhydride (30 g) were charged, and the resultant mixture was stirred at 80°–100° C. for 3 hours. After completion of the reaction, the reaction mixture was subjected to the same work-up as in Example 2 to give 16.2 g of dl-3-acetoxy-2,3-dimethyl-4-cyclopentenone. Yield, 96.5%. B.P., 52°–55° C./0.4–0.5 mmHg).

The thus obtained dl-3-acetoxy-2,3-dimethyl-4-cyclopentenone (2 g), Porcine Liver Esterase (manufactured by Sigma Inc.) (100 mg) and 0.1 M phosphate buffer (100 ml; pH 7) were mixed together, and the resultant mixture was stirred at 25°–30° C. for 24 hours. After completion of the reaction, the reaction mixture was extracted with methyl isobutyl ketone (50 ml) three times. After completion of the reaction, the solvent was removed from the extract, and the residue was extracted with a mixture of ethyl acetate and toluene (3:5) and purified by colum chromatography to give 0.46 g of l-3-hydroxy-2,3-dimethyl-4-cyclopentenone (yield, 31%; optical rotation, $[α]_D^{20}$ −24.3° (c=1, chloroform); $n_D^{20}$ 1.4765) and 1.24 g of l-3-acetoxy-2,3-dimethyl-4-cyclopentenone (optical rotation, $[a]_D^{20}$ −20.7° (c=1, chloroform); $n_D^{20}$ 1.4697).

The above obtained l-3-hydroxy-2,3-dimethyl-4-cyclopentenone (0.3 g), triethylamine (3 g) and water (0.3 g) were mixed together while stirring at 30° C. for 48 hours. After completion of the reaction, the resultant mixture was extracted with methyl isobutyl ketone (15 ml) three times. The extracts were combined together and washed with an aqueous solution of 0.5 N hydrochloric acid and water in this order. The washed extract was concentrated, and the residue was purified by chromatography using a mixture of toluene and ethyl acetate (5:3) to give 0.28 g of S(+)-4-hydroxy-2,3-dimethyl-2-cyclopentenone. Optical purity, 86%. $[α]_D^{20}$ +19.3° (c=1, chloroform). $n_D^{20}$ 1.5070.

EXAMPLE 6 dl-3-Acetoxy-2-allyl-3-methyl-4-cyclopentenone (1 g), esterase (manufactured by Sigma Inc., from wheat germ) (0.2 g) and 0.1 M phosphate buffer (10 ml; pH 7) were mixed together, and the resultant mixture was stirred at 20°–30° C. for 35 hours. After completion of the reaction, the reaction mixture was extracted with methyl isobutyl ketone (10 ml) three times. The solvent was removed from the extract, and the residue was purified by column chromatography using a mixture of ethyl acetate and toluene (3:5) to give 0.18 g of l-2-allyl-3-hydroxy-3-methyl-4-cyclopentenone.

The thus obtained l-2-allyl-3-hydroxy-3-methyl-4-cyclopentenone (0.15 g) and 0.1 M carbonate buffer (5 ml; pH 11.5) were mixed together, and the resultant mixture was stirred at 0°–5° C. for 24 hours and at 20° C. for 24 hours. After completion of the reaction, the reaction mixture was extracted with methyl isobutyl ketone (10 ml) four times. The extracts were combined together and concentrated. The residue was purified with a mixture of toluene and ethyl acetate (5:2) to give 0.14 g of S(+)-2-allyl-3-methyl-4-hydroxy-2-cyclopentenone. Optical purity, 78.7%.

EXAMPLE 7

Into a 500 ml Sakaguchi's flask, a liquid nutrient medium (composition: glucose, 1%; yeast extract, 0.3%; malt extract, 0.3%; polypeptone, 0.5%; pH, 5.6) (200 ml) was charged. After sterilization, *Candida krusei* OUT-6007 was inoculated therein and cultured at 30° C. for 2 days under shaking. dl-3-Acetoxy-2-allyl-3-methyl-4-cyclopentenone (4 g) was added thereto, and fermentation under shaking was continued at 30° C. for 24 hours for hydrolysis. After completion of the reaction, the resultant mixture was subjected to centrifugation, and the supernatant was extracted with methyl isobutyl ketone (70 ml) four times. The extracts were combined together and concentrated. The residue was purified by column chromatography using a mixture of ethyl acetate and toluene (3:5) as an eluent to give 1.5 g of l-2-allyl-3-hydroxy-3-methyl-4-cyclopentenone (yield, 48%; optical rotatoin, $[\alpha]_D^{20} -21.7°$ (c=1, chloroform)) and 1.96 g of l-3-acetoxy-2-allyl-3-methyl-4-cyclopentenone (optical rotation, $[\alpha]_D^{20} -82.6°$ (c=1, chloroform)).

The thus obtained l-2-allyl-3-hydroxy-3-methyl-4-cyclopentenone (0.5 g), triethylamine (4 ml) and water (0.5 g) were mixed together, and the resultant mixture was stirred at 20°–30° C. for 48 hours. After completion of the reaction, the reaction mixture was subjected to the same work-up as in Example 6 to give 0.46 g of S(+)-2-allyl-4-hydroxy-3-methyl-2-cyclopentenone. Optical purity, 89.5%.

EXAMPLE 8

Into a 500 ml Sakaguchi's flask, a liquid nutrient medium (composition: glucose, 1%; yeast extract, 0.5%; peptone, 0.1%; K$_2$HPO$_4$, 0.05%; pH, 5.6) (200 ml) was charged. After sterilization, *Pseudomonas fragi* IFO-3458 was inoculated therein and cultured at 30° C. for 2 days under shaking. dl-3-Acetoxy-2-allyl-3-methyl-4-cyclopentenone (1.5 g) was added thereto, and fermentation under shaking was continued at 30° C. for 24 hours for hydrolysis. After completion of the reaction, the resultant mixture was extracted with methyl isobutyl ketone (50 ml) four times. The extracts were combined together and concentrated. The residue was purified by column chromatography using a mixture of ethyl acetate and toluene (3:5) as an eluent to give 0.28 g of d-2-allyl-3-hydroxy-3-methyl-4-cyclopentenone (yield, 24%; optical rotation, $[\alpha]_D^{20} +22.5°$ (c=1, chloroform); $n_D^{20} 1.4978$) and 0.75 g of d-3-acetoxy-2-allyl-3-methyl-4-cyclopentenone (optical rotation, $[\alpha]_D^{20} +80.7°$ (c=1, chloroform); $n_D^{20} 1.4801$).

The thus obtained d-2-allyl-3-hydroxy-3-methyl-4-cyclopentenone (0.25 g), triethylamine (2 ml), alumina (5 g) and benzene (20 ml) were mixed together, and the resultant mixture was heated at 50°–60° C. for 10 hours. After completion of the reaction, the reaction mixture was subjected to the same work-up as in Example 1 to give 0.2 g of R(-)-2-allyl-4-hydroxy-3-methyl-2-cyclopentenone. Optical purity, 94%. $[\alpha]_D^{20} -14.1°$ (c=1, chloroform). $n_D^{20} 1.5158$.

EXAMPLE 9

In the same manner as in Example 8 but using 1.25 g of l-3-acetoxy-2-allyl-3-methyl-4-cyclopentenone obtained in Example 1 instead of dl-3-acetoxy-2-allyl-3-methyl-4-cyclopentenone, the reaction was carried out as in Example 8, whereby 0.59 g of d-2-allyl-3-hydroxy-3-methyl-4-cyclopentenone was obtained. Yield, 60%. $[\alpha]_D^{20} +23.6°$ (c=1, chloroform). $n_D^{20} 1.4984$.

The thus obtained d-2-allyl-3-hydroxy-3-methyl-4-cyclopentenone (0.5 g), alumina (15 g), triethylamine (4 ml) and benzene (25 ml) were mixed together and heated at 50°–60° C. for 8 hours. The same work-up as in Example 8 gave 0.42 g of R(-)-2-allyl-4-hydroxy-2-3-methyl-2-cyclopentenone. Optical purity, 95%.

EXAMPLE 10

To a solution of dl-2-allyl-3-hydroxy-3-methyl-4-cyclopentenone (3.1 g) and pyridine (9.3 g) in dichloromethane (15.5 g), octanoyl chloride (7.7 g) was dropwise added at 10°–20° C. in 3 hours, and the resultant mixture was allowed to react at 20°–30° C. for 25 hours. After completion of the reaction, water (10 ml) was added thereto while keeping the temperature below 10° C. From the resulting mixture, the organic layer was separated and washed with a 1% aqueous sodium chloride solution, a 1% sodium bicarbonate solution and water in order. The solvent was removed from the organic layer, and the residue was purified by chromatography using a mixture of toluene and ethyl acetate (10:1) to give 4.64 g of dl-2-allyl-3-octanoyloxy-3-methyl-2-cyclopentenone. Yield, 91%. $n_D^{20} 1.4757$.

In the same manner as in Example 8 but using dl-2-allyl-3-octanoyloxy-3-methyl-2-cyclopentenone (2.0 g) instead of dl-3-acetoxy-2-allyl-3-methyl-4-cyclopentenone, there was obtained 0.3 g of l-2-allyl-3-hydroxy-3-methyl-4-cyclopentenone.

The thus obtained l-2-allyl-3-hydroxy-3-methyl-4-cyclopentenone (0.2 g), triethylamine (1.5 ml), alumina (4 g) and benzene (15 ml) were mixed together, and the resultant mixture was heated at 50°–60° C. for 10 hours. After completion of the reaction, the reaction mixture was subjected to the same work-up as in Example 1 to give 0.15 g of S(+)-2-allyl-4-hydroxy-3-methyl-2-cyclopentenone. Optical purity, 76%.

EXAMPLE 11

In the same manner as in Example 8 but using dl-3-acetoxy-2-n-pentyl-3-methyl-4-cyclopentenone (2 g), the fermentation under shaking was continued at 30° C. for 30 hours for hydrolysis, and the supernatant was extracted with methyl isobutyl ketone (40 ml) twice.

The same work-up as in Example 8 gave 0.48 g of d-3-hydroxy-2-n-pentyl-3-methyl-4-cyclopentenone (yield, 30%; optical rotation, [60 ]$_D^{20}$+17.5° (c=1, chloroform); n$_D^{20}$ 1.4811) and 0.86 g of d-3-acetoxy-2-n-pentyl-3-methyl-4-cyclopentenone (optical rotation, [α]$_D^{20}$+60.8° (c=1, chloroform); n$_D^{20}$ 1.4703).

d-3-Hydroxy-2-n-pentyl-3-methyl-4-cyclopentenone as obtained above (0.4 g), triethylamine (4 ml) and water (0.2 g) were mixed together, and the resultant mixture was stirred at 30°–40° C. for 20 hours. The reaction mixture was subjected to the same work-up as in Example 8 to give 0.33 g of R(—)-4-hydroxy-2-n-pentyl-3-methyl-2-cyclopentenone. Optical purity, 88%. [α]$_D^{20}$—16.3° (c=1, chloroform). n$_D^{20}$ 1.4879.

EXAMPLE 12

In the same manner as in Example 8 but using dl-3-acetoxy-2-propargyl-3-methyl-4-cyclopentenone (1.5 g) instead of dl-3-acetoxy-2-allyl-3-methyl-4-cyclopentenone, the reaction was carried out to give 0.19 g of d-3-hydroxy-2-propargyl-3-methyl-4-cyclopentenone (yield, 16%; optical rotation, [α]$_D^{20}$+124° (c=1, chloroform); n$_D^{20}$ 1.5013) and 0.82 g of d-3-acetoxy-2-propargyl-3-methyl-4-cyclopentenone (optical rotation, [α]$_D^{20}$+14.6° (c=1, chloroform); n$_D^{20}$ 1.4943).

In the same manner as in Example 3, d-3-hydroxy-2-propargyl-3-methyl-4-cyclopentenone as obtained above (0.15 g) was rearranged to 0.09 g of R(—)-4-hydroxy-2-propargyl- 3-methyl-2-cyclopentenone. Optical purity, 93%. [α]$_D^{20}$—19.2° (c=1, chloroform). n$_D^{20}$ 1.5302.

EXAMPLES 14 TO 16

In the same manner as in Example 7 but using the microorganism as shown in Table 1 instead of *Candida krusei* OUT-6007, the reaction was carried out. The results are shown in Table 1.

TABLE 1

| Example No. | Microorganism | Hydrolysis Yield of l-2-allyl-3-hydroxy-3-methyl-4-cyclopentenone (g) | Rearrangement Yield of S(+)-2-allyl-4-hydroxy-3-methyl-2-cyclopentenone (Optical purity) (%) |
|---|---|---|---|
| 14 | *Hansenula anomala* var. cifferrii OUT-6095 | 1.63 | 90 (88.2) |
| 15 | *Metshnikowia pulcherwina* IFO-0561 | 1.25 | 90.5 (82.7) |
| 16 | *Pleurotus ostreatus* IFO-7051 | 0.96 | 86.5 (92.3)(*) |

Note:
(*)The reaction was carried out as in Example 1.

EXAMPLE 17 TO 19

In the same manner as in Example 1 but using the hydrolase as shown in Table 2 instead of Porcine Liver esterase, the reaction was carried out. The results are shown in Table 2.

TABLE 2

| Example No. | Hydrolase Name | Reaction condition Amount (g) | Temperature (°C.) | Time (hr) | Hydrolysis Yield of l-2-allyl 3-hydroxy-3-methyl-cyclopentenone (g) | Rearrangement Yield of S(+)-2-allyl-4-hydroxy-3-methyl-2-cyclo-pentenone (Optical purity) (%) |
|---|---|---|---|---|---|---|
| 17 | Cholesterol(*1) esterase | 0.2 | 25–30 | 30 | 0.21 | 85 (92.4) |
| 18 | Esterase(*2) | 1 | 25–30 | 30 | 0.2 | 87 (81.2) |
| 19 | Steapsin(*3) | 1 | 25–30 | 40 | 0.06 | 94.2 (72.9)(*4) |

Note:
(*1)Produced from *Schizophyllum commune*: Toyo Boseki K. K.
(*2)Produced from *Candida cylindracea*. Sigma Inc.
(*3)Wako Pure Chemical Industries, Ltd.
(*4)The reaction was carried out as in Example 6.

EXAMPLE 13

In the same manner as in Example 8 but using dl-3acetoxy-2-ω-butentyl-3-methyl-4-cyclopentenone (2 g), the fermentation under shaking was continued at 30° C. for 20 hours for hydrolysis, and the supernatant was extracted with methyl isobutyl ketone (40 ml) twice. The same work-up as in Example 8 gave 0.32 g of d-3-hydroxy-2-ω-butentyl-3-methyl-4-cyclopentenone (yield, 20%; optical rotation, [α]$_D^{20}$+21.1° (c=1, chloroform); n$_D^{20}$ 1.4983) and 1.02 g of d-3-acetoxy-2-ω-butentyl-3-methyl-4-cyclopentenone (optical rotation, [α]$_D^{20}$+62° (c=1, chloroform); n$_D^{20}$ 1.4806).

d-3-Hydroxy-2-ω-butentyl-3-methyl-4-cyclopentenone as obtained above (0.25 g), triethylamine (0.5 g), alumina (5 g) and benzene (15 ml) were mixed together, and the resultant mixture was stirred at 50°–60° C. for 6 hours. The reaction mixture was subjected to the same work-up as in Example 2 to give 0.22 g of R(—)-4-hydroxy-2-ω-butentyl-3-methyl-2-cyclopentenone. Optical purity, 92%. [α]$_D^{20}$—13.7° (c=1, chloroform). n$_D^{20}$ 1.5170.

EXAMPLE 20

In the same manner as in Example 8 but using *Pseudomonas fluoresens* IFO-3903 instead of *Pseudomonas fragi* IFO-3458 as well as using l-3-acetoxy-2-allyl-3-methyl-4-cyclopentenone (1.0 g) obtained in Example 1 instead of dl-3-acetoxy-2-allyl-3-methyl-4-cyclopentenone, the reaction was carried out to give 0.17 g of d-2-allyl-3-hydroxy-3-methyl-4-cyclopentenone. Yield, 22%.

The thus obtained d-2-allyl-3-hydroxy-3-methyl-4-cyclopentenone (0.1 g), alumina (10 g) and water (20 ml) were mixed together, and the resultant mixture was stirred at 20°–30° C. for 10 hours and at 30°–40° C. for 10 hours. Alumina was collected by filtration and washed with methanol (10 ml) twice. The filtrate was concentrated under reduced pressure. The residue was purified by chromatography to give 0.8 g of R(—)-2-allyl-4-hydroxy-3-methyl-2-cyclopentenone. Optical purity, 83%.

EXAMPLES 21 TO 23

In the same manner as in Example 14 but using the starting material as shown in Table 3 instead of dl-3-acetoxy-2-allyl-3-methyl-4-cyclopentenone, the reaction was carried out. The results are shown in Table 3.

TABLE 3

| Example No. | Hydrolysis | | | | Rearrangement | | |
|---|---|---|---|---|---|---|---|
| | Starting material | | Product | | | | Optical |
| | Name | Amount (g) | Name | Yield (g) | Name | Yield (%) | putity (%) |
| 21 | dl-3-Acetoxy-2-n-pentyl-3-methyl-4-cyclopentenone | 3 | l-3-Hydroxy-2-n-pentyl-3-methyl-4-cyclopentenone | 1.12 | S(+)-4-Hydroxy-2-n-pentyl-3-methyl-2-cyclopentenone | 88 | 85.2 |
| 22 | dl-3-Acetoxy-2-(ω-butentyl)-3-methyl-4-cyclopentenone | 3 | l-3-Hydroxy-2-(ω-butentyl)-3-methyl-4-cyclopentenone | 1.01 | S(+)-4-Hydroxy-2-(ω-butentyl)-3-methyl-2-cyclopentenone | 89.5 | 87 |
| 23 | dl-3-Acetoxy-2-propargyl-3-methyl-4-cyclopentenone | 3 | l-3-Hydroxy-2-propargyl-3-methyl-4-cyclopentenone | 0.84 | S(+)-4-Hydroxy-(*)-2-propargyl-3-methyl-2-cyclopentenone | 62 | 90.6 |

Note:
(*)The reaction was carried out as in Example 3.

EXAMPLES 24 TO 27

Rearrangement of l-2-allyl-3-hydroxy-3-methyl-4-cyclopentenone to S(+)-2-allyl-4-hydroxy-3-methyl-2-cyclopentenone was carried out as in Example 1 but under the reaction condition as shown in Table 4. The results are shown in Table 4.

TABLE 4

| Example No. | Amount of l-2-allyl-3-hydroxy-3-methyl-4-cyclopentenone (g) | Base or catalyst | | Reaction condition | | S(+)-2-Allyl-4-hydroxy-3-methyl-2-cyclopentenone | |
|---|---|---|---|---|---|---|---|
| | | Name | Amount (g) | Temp. (°C.) | Time (hr) | Yield (%) | Optical purity (%) |
| 24 | 0.3 | N—methylmorpholine | 2.5 | 60–80 | 7 | 72 | 89 |
| | | Water | 0.3 | | | | |
| 25 | 0.3 | Alumina | 5 | 40 | 10 | 87 | 82.6 |
| | | Water | 15 | | | | |
| 26 | 0.3 | Triethylamine | 9 | 50–70 | 8 | 82 | 92.6 |
| | | Water | 0.1 | | | | |
| 27 | 0.3 | 0.1 M Carbonate buffer (pH, 10.5) | 5 | 20–30 | 48 | 93 | 88.6 |

EXAMPLE 28

Into a flask equipped with a stirrer and a thermometer, dl-3-hydroxy-2-n-pentyl-4-cyclopentenone (16.8 g), p-toluenesulfonic acid (0.1 g) and acetic anhydride (33.6 g) were charged, and the resultant mixture was stirred at 100° C. for 2 hours. After completion of the reaction, acetic anhydride was removed under reduced pressure, and the residue was extracted with toluene. The toluene layer was washed with 1% sodium bicarbonate solution and water. Toluene was removed from the toluene layer to give dl-3-acetoxy-2-n-pentyl-4-cyclopentenone (19.5 g). Yield, 93%. B.P., 105°–110° C./0.2–0.5 mmHg.

The thus obtained dl-3-acetoxy-2-n-pentyl-4-cyclopentenone (5 g), Lipase P-30A (manufactured by Amano Pharmaceuticals Co..) (100 mg) and 0.1 M phosphate buffer (200 ml; pH 7.0) were mixed together, and the resultant mixture was vigorously stirred at 25°–30° C. for 20 hours. After completion of the reaction, the reaction mixture was extracted with methyl isobutyl ketone (50 ml) four times. The extracts were combined together and concentrated. The residue was purified by column chromatography using a mixture of ethyl acetate and toluene (3:5) as an eluent to give 1.8 g of l-3-hydroxy-2-n-pentyl-4-cyclopentenone (yield, 45%; optical rotation, $[\alpha]_D^{20} -53.3°$ (c=1, chloroform)) and 2.54 g of d-3-acetoxy-2-n-pentyl-4-cyclopentenone (optical rotation, $[\alpha]_D^{20} +112.0°$ (c=1, chloroform)).

The above obtained l-3-hydroxy-2-n-pentyl-4-cyclopentenone (0.5 g), alumina (10 g) and benzene (30 ml) were mixed together while stirring at 40°–50° C. for 6 hours. Alumina was collected by filtration and washed with methanol (10 ml) twice. The filtrate was concentrated, and the residue was purified by column chromatography using a mixture of toluene and ethyl acetate (5:3) to give 0.46 g of R(+)-4-hydroxy-2-n-pentyl-2-cyclopentenone. Optical rotation, $[\alpha]_D^{20} +12.9°$ (c=1, chloroform).

EXAMPLE 29

In a flask, dl-2-allyl-3-hydroxy-4-cyclopentenone (13.8 g), toluenesulfonic acid (0.1 g) and acetic anhydride (27.6 g) were charged, and the resultant mixture was heated at 90°–100° C. for 3 hours. The reaction mixture was treated as in Example 28 to give 16.0 g of dl-3-acetoxy-2-allyl-4-cyclopentenone. Yield, 89%. B.P., 80°–85° C./0.6–1 mmHg.

The thus obtained dl-3-acetoxy-2-allyl-4-cyclopentenone (5.5 g), Lipase PL (manufactured by Meito Sangyo K.K.) (0.2 g) and 0.1 M phosphate buffer (250 ml;

pH 7.0) were mixed together, and the resultant mixture was vigorously stirred at 25°-35° C. for 24 hours. After completion of the reaction, the reaction mixture was treated as in Example 1 to give 1.68 g of l-2-allyl-3-hydroxy-4-cyclopentenone (yield, 40%; optical rotation $[\alpha]_D^{20} -28.2°$ (c=1, chloroform)) and 2.86 g of d-3-acetoxy-2-allyl-4-cyclopentenone (optical rotation $[\alpha]_D^{20} +68.8°$ (c=1, chloroform)).

The above obtained l-2-allyl-3-hydroxy-4-cyclopentenone (0.5 g), pyridine (0.2 g), alumina (8 g) and benzene (30 ml) were mixed together while stirring at 30°-50° C. for 10 hours. Alumina was collected by filtration and washed with methanol (10 ml) twice. The filtrate was concentrated, and the residue was purified by column chromatography using a mixture of toluene and ethyl acetate (5:3) to give 0.44 g of R(+)-2-allyl-4-hydroxy-2-cyclopentenone. Optical rotation, $[\alpha]_D^{20} +19.2°$ (c=1, chloroform).

EXAMPLE 30 dl-3-acetoxy-2-n-pentyl-4-cyclopentenone (3 g), Lipase Godo BSL (manufactured by Godo Shusei K.K.) (150 mg) and 0.1 M phosphate buffer (120 ml; pH 7.0) were mixed together, and the resultant mixture was vigorously stirred at 30° C. for 20 hours. After completion of the reaction, the reaction mixture was treated as in Example 28 to give 1.01 g of l-3-hydroxy-2-n-pentyl-4-cyclopentenone (yield, 42%; optical rotation, $[\alpha]_D^{20} -51.6°$ (c=1, chloroform)) and 1.54 g of d-3-acetoxy-2-n-pentyl-4-cyclopentenone (optical rotation, $[\alpha]_D^{20} +107.5°$ (c=1, chloroform)).

The above obtained l-3-hydroxy-2-n-pentyl-4-cyclopentenone (0.5 g), triethylamine (4 ml) and water (0.5 g) were mixed together while stirring at 10°-25° C. for 48 hours. After completion of the reaction, the resultant mixture was extracted with methyl isobutyl ketone (20 ml) three times. The extracts were combined together and concentrated. The residue was purified by chromatography to give 0.44 g of R(+)-4-hydroxy-2-n-pentyl-2-cyclopentenone. Optical rotation, $[\alpha]_D^{20} +11.9°$ (c=1, chloroform).

EXAMPLES 31 AND 32

Rearrangement of l-2-allyl-3-hydroxy-4-cyclopentenone to R(+)-2-allyl-4-hydroxy-2-cyclopentenone was carried out as in Example 28 but under the reaction condition as shown in Table 5. The results are shown in Table 5.

TABLE 5

| Example No. | Amount of l-2-allyl-3-hydroxy-4-cyclo-pentanone (g) | Base or catalyst Name | Amount (g) | Reaction condition Temp. (°C.) | Time (hr) | R(+)-2-Allyl-4-hydroxy-2-cyclopentenone Yield (%) | Optical Rotation $[\alpha]_D^{20}$ |
|---|---|---|---|---|---|---|---|
| 31 | 0.3 | Alumina | 5 | 40 | 15 | 86 | 17.3° |
|    |     | Water | 15 |    |    |    |       |
| 32 | 0.3 | 0.1 M Carbonate buffer (pH, 11.0) | 5 | 20-30 | 48 | 91 | 18.2° |

EXAMPLE 33 dl-3-Acetoxy-2-propargyl-4-cyclopentenone (3 g), Lipase M-AP (manufactured by Amano Pharmaceutical Co.) (50 mg) and 0.1 M phosphate buffer (100 ml; pH 6.0) were mixed together, and the resultant mixture was vigorously stirred at 25°-35° C. for 20 hours. After completion of the reaction, the reaction mixture was extracted with hexane (50 ml) three times. The extracts were combined together and concentrated under reduced pressure. The residue was purified by column chromatography using a mixture of ethyl acetate and toluene (1:10) to give 1.68 g of d-3-acetoxy-2-propargyl-4-cyclopentenone (optical rotation, $[\alpha]_D^{20} +82.9°$ (c=1, chloroform); $n_D^{25}$ 1.5042). The remaining aqueous layer after extraction with hexane was extracted with methyl isobutyl ketone (50 ml) four times. The extracts were combined together and concentrated under reduced pressure to give 0.99 g of l-3-hydroxy-2-propargyl-4-cyclopentenone (yield, 42.2%; optical rotation, $[\alpha]_D^{20} -42.6°$ (c=1, chloroform); $n_D^{25}$ 1.5258).

EXAMPLE 34 l-3-hydroxy-2-propargyl-4-cyclopentenone as obtained in Example 33 (0.9 g) was dissolved in a mixture of pyridine and water (1:10 by volume) (10 ml), and basic alumina (3 g) was added thereto. The resultant mixture was allowed to react at 30° C. for 24 hours. After completion of the reaction, alumina was collected by filtration. The filtrate was neutralized with 1N aqueous hydrochloric acid and extracted with methyl isobutyl ketone (10 ml) four times. The oily extracts were combined together and concentrated. The residue was purified by column chromatography to give 0.7 g of R(+)-4-hydroxy-2-propargyl-2-cyclopentenone. Optical rotation, $[\alpha]_D^{20} +9.4°$ (c=1, chloroform). $n_D^{20}$ 1.5184.

IR: 1715 cm$^{-1}$(CO). NMR (CDCl$_3$, 90 MHz, internal standard TMS): 7.35 (1H), 4.62 (broad d, 1H), 4.02 (broad s, 1H), 3.02 (d, 2H), 2.4–2.65 (multi, 2H), 1.98 (s, 1H).

What is claimed is:

1. A process for preparing an optically active 4-hydroxy-2-cyclopentenone of the formula:

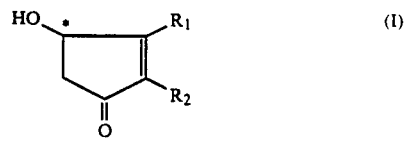

(I)

wherein R$_1$ is a hydrogen atom or a methyl group, R$_2$ is an alkyl group of not more than 12 carbon atoms, an alkenyl group of not more than 12 carbon atoms or an alkenyl group of not more than 12 carbon atoms and the asterisk (*) indicates an asymmetric configuration, which comprises subjecting a racemic or optically active 4-cyclopentenone ester of the formula:

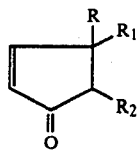

wherein $R_1$ and $R_2$ are each as defined above, R is a lower alkanoyloxy group and the substitutents $R_1$ and $R_2$ take a cis-configuration to asymmetric hydrolysis with an enzyme or microorganism capable of hydrolyzing the same, and treating the resultant optically active 4-cyclopentenone-alcohol of the formula:

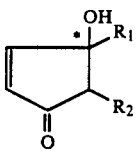

wherein $R_1$ and $R_2$ are each as defined above, the asterisk (*) indicates an asymmetric configuration and the substituents $R_1$ and $R_2$ take a cis-configuration with a catalyst selected from the group consisting of organic tertiary amines, metal oxides, inorganic bases and basic buffers at a temperature of −20° to 130° C., whereby the optically active 4-cyclopentenone-alcohol (II) is rearranged to the optically active 4-hydroxy-2-cyclopentenone (I) while maintaining the original steric configuration.

2. The process according to claim 1, wherein the 4-cyclopentenone ester is prepared by reacting a racemic 4-cyclopentenone-alcohol of the formula:

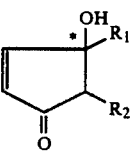

wherein $R_1$ and $R_2$ are each as defined above and the substituents $R_1$ and $R_2$ take a cis-configuration with an aliphatic carboxylic acid or its reactive derivative.

3. The process according to claim 1, wherein the optically acitve 4-cyclopentenone-alcohol is prepared by subjecting a racemic 4-cyclopentenone ester of the formula:

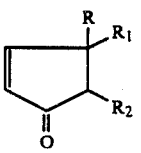

wherein $R_1$ and $R_2$ are each as defined above, R is a lower alkanoyloxy group and the substitutents $R_1$ and $R_2$ take a cis-configuration to asymmetric hydrolysis with an enzyme or microorganism, separating the unhydrolyzed optical isomer of the 4-cyclopentenone ester and subjecting the recovered unhydrolyzed optical isomer to hydrolysis with an enzyme or microorganism.

4. The process according to claim 1, wherein $R_1$ is methyl.

5. The process according to claim 4, wherein the optically active 4-cyclopentenone-alcohol is the l-form and the optically active 4-hydroxy-2-cyclopentenone is the S(+)-form.

6. The process according to claim 4, wherein the optically active 4-cylopentenone-alcohol is the d-form and the optically active 4-hydroxy-2-cyclopentenone is the R(−)-form.

7. The process according to claim 4, wherein the optically active 4-cyclopentenone ester is the d-form, the optically active 4-cyclopentenone-alcohol is the l-form and the optically active 4-hydroxy-2-cyclopentenone is the S(+)-form.

8. The process according to claim 4, wherein the optically active 4-cyclopentenone ester is the l-form, the optically active 4-cyclopentenone-alcohol is the d-form and the optically active 4-hydroxy-2-cyclopentenone is the R(−)-form.

9. The process according to claim 1, wherein the catalyst is an organic tertiary amine selected from the group consisting of triethylamine, N-methylmorpholine, N-methylpiperidine, N,N'-dimethylpiperazine, pyridine and lutidine.

10. The process according to claim 1, wherein $R_1$ is hydrogen.

11. The process according to claim 10, wherein the optically active 4-cyclopentenone-alcohol is the l-form and the optically active 4-hydroxy-2-cyclopentenone is the R(+)-form.

12. The process according to claim 10, wherein the optically active 4-cyclopentenone ester is the d-form, the optically active 4-cyclopentenone-alcohol is the d-form and the optically active 4-hydroxy-2-cyclopentenone is the S(−)-form.

13. The process according to claim 1, wherein the catalyst is a metal oxide selected from the group consisting of alumina and silica gel.

14. The process according to claim 1, wherein the catalyst is an inorganic base selected from the group consisting of sodium hydroxide, potassium hydroxide, sodium carbonate, potassium carbonate, sodium hydrogencarbonate, potassium hydrogencarbonate and potassium monohydrogen phosphate.

15. The process according to claim 1, wherein the catalyst is a basic buffer selected from the group consisting of carbonate buffers, phosphate buffers and borate buffers.

16. The process according to claim 1, wherein the catalyst is used in an amount of 0.05 to 60 parts by weight to one part by weight of the optically active 4-cyclopentenone-alcohol.

17. The process according to claim 1, wherein the enzyme is obtained from a microorganism which is a member selected from the group consisting of Rhodotorula, Trichoderma, Candida, Pseudomonas, Hansenula, Bacillus, Achromobacter, Nocardia, Chromobacterium, Flavobacterium, Rhizopus, Mucor, Aspergillus, Alcaligenes, Torulopsis, Corynebacterium, Endomyces, Saccharomyces, Arthrobacter, Metshnikowia, Pleurotus, Streptomyces, Proteus, Gliocladium, Acetobacter, Helminthosporium, Brevibacterium, Escherichia, Citrobacter, Micrococcus, Pediococcus, Klebsiella, Absidia, Geotrichem, Streptomyces, Lactobacillus, Cryptococcus, Pichia, Aureobasidium, Actimomucor, Enterobacter, Microbacterium, Penicillium and Schizophyllum.

18. The process according to claim 17, wherein the enzyme is obtained from a microorganism belonging to Pseudomonas.

19. The process according to claim 18, wherein the microorganism is *Pseudomonas fragi, Pseudomonas fluorescens* or *Pseudomonas aeruginosa.*

20. The process according to claim 17, wherein the enzyme is obtained from a microorganism belonging to Trichoderma, Candida, Hansenula, Bacillus, Achromobacter, Nocardia, Chromobacterium, Flavobacterium, Torulopsis, Metshnikowia, Pleurotus or Schizophyllum.

21. The process according to claim 20, wherein the microorganisim is *Candida cylindracea, Hansenula anomala var. ciferrii, Metshnikowia pulcherrima, Pleurotus ostreatus, Schizophyllum commune, Candida krusei, Bacillus subtilis, Achromobacter parvulus, Flavobacterium lutesens, Chromobacterium iodinum, Nocardia uniformis subptsuyamanenus, Torulopsis ernobii* or *Trichoderma longibrachiatum.*

22. The process according to claim 1, wherein the microorganism is a member selected from the group consisting of Rhodotorula, Trichoderma, Candida, Pseudomonas, Hansenula, Bacillus, Achromobacter, Nocardia, Chromobacterium, Flavobacterium, Rhizopus, Mucor, Aspergillus, Alcaligenes, Torulopsis, Corynebacterium, Endomyces, Saccharomyces, Arthrobacter, Metshnikowia, Pleurotus, Streptomyces, Proteus, Gliocladium, Acetobacter, Helminthosporium, Brevibacterium, Escherichia, Citrobacter, Micrococcus, Pediococcus, Klebsiella, Absidia, Geotrichem, Streptomyces, Lactobacillus, Cryptococcus, Pichia, Aureobasidium, Schizophyllum, Actimomucor, Enterobacter, Microbacterium and Penicillium.

23. The process according to claim 22, wherein the microorganism is the one belonging to Pseudomonas.

24. The process according to claim 22, wherein the microorganism is *Pseudomonas fragi, Pseudomonas fluorescens* or *Pseudomonas aeruginosa.*

25. The process according to claim 22, wherein the microorganism is one belonging to Trichoderma, Candida, Hansenula, Bacillus, Achromobacter, Nocardia, Chromobacter, Flavobacterium, Torulopsis, Metshnikowia, Pleurotus or Schizophyllum.

26. The process according to claim 25, wherein the microorganism is *Candida cylindracea, Hansenula anomala var. ciferrii, Metshnikowia pulcherrima, Pleurotus octreatus, Schizophyllum commune, Candida krusei, Bacillus subtilis, Achromobacter parvulus, Flavobacterium lutesens, Chromobacterium iodinum, Nocardia uniformis subptsyamanenus, Torulopsis ernobii* or *Trichoderma longibrachiatum.*

27. A process for preparing an optically active 4-hydroxy-2-cyclopentenone of the formula:

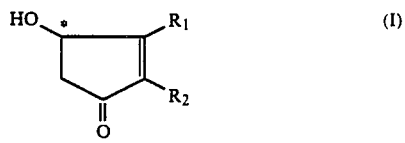

wherein $R_1$ is a hydrogen atom or a methyl group, $R_2$ is methyl, ethyl, n-propyl, isopropyl, n-butyl, sec-butyl, t-butyl, iso-butyl, n-pentyl, isopentyl, n-hexyl, cyclopentyl, cyclohexyl, allyl, 2-butenyl, 3-butenyl, 2-pentynyl, n-hexyl, n-heptyl, 2-pentenyl, 3-hexynyl, propargyl or 2-methylallyl, and the asterisk (*) indicates an asymmetric configuration, which comprises subjecting a racemic or optically active 4-cyclopentenone ester of the formula:

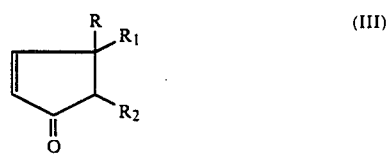

wherein $R_1$ and $R_2$ are each as defined above, R is a lower alkanoyloxy group and the substituents $R_1$ and $R_2$ take a cis-configuration to asymmetric hydrolysis with an enzyme or microorganism capable of hydrolyzing the same, and treating the resultant optically active 4-cyclopentenone-alcohol of the formula:

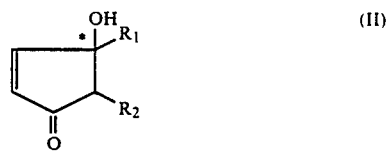

wherein $R_1$ and $R_2$ are each as defined above, the asterisk (*) indicates an asymmetric configuration and the substitutents $R_1$ and $R_2$ take a cis-configuration with a catalyst selected from the group consisting of organic teritiary amines, metal oxides, inorganic bases and basic buffers at a temperature of −20° to 130° C., whereby the optically active 4- cyclopentenone-alcohol (II) is rearranged to the optically active 4-hydroxy-2-cyclopentenone (I) while maintaining the original steric configuration.

* * * * *